US008641652B2

(12) United States Patent
Gazayerli

(10) Patent No.: US 8,641,652 B2
(45) Date of Patent: Feb. 4, 2014

(54) GARMENT WITH LUMBAR TRACTION DEVICE

(76) Inventor: M. Mounir Gazayerli, Bloomfield Hills, MI (US)

( * ) Notice: Subject to any disclaimer, the term of this patent is extended or adjusted under 35 U.S.C. 154(b) by 0 days.

(21) Appl. No.: 13/345,312

(22) Filed: Jan. 6, 2012

(65) Prior Publication Data

US 2012/0123310 A1 May 17, 2012

Related U.S. Application Data

(63) Continuation-in-part of application No. 12/944,234, filed on Nov. 11, 2010, now Pat. No. 8,535,254.

(60) Provisional application No. 61/260,649, filed on Nov. 12, 2009.

(51) Int. Cl.

| | |
|---|---|
| ***A61F 5/00*** | (2006.01) |
| ***A61F 5/042*** | (2006.01) |
| ***A63B 21/02*** | (2006.01) |
| ***A61H 1/00*** | (2006.01) |

(52) U.S. Cl.
USPC ................ 602/36; 602/32; 128/876; 482/124

(58) Field of Classification Search
USPC ............................ 602/32–40; 601/23, 33–35; 482/121–131, 907, 140, 78–80, 82, 482/139; 2/69, 79, 227, 271, 233, 312, 338; 128/876
See application file for complete search history.

(56) References Cited

U.S. PATENT DOCUMENTS

| | | | | |
|---|---|---|---|---|
| 1,969,165 | A | 8/1934 | Turner | |
| 3,134,379 | A * | 5/1964 | Nightingale | 602/32 |
| 4,865,022 | A | 9/1989 | Gorsen | |
| 4,910,802 | A * | 3/1990 | Malloy | 2/69 |
| 5,256,119 | A * | 10/1993 | Tudor | 482/74 |
| 5,308,305 | A * | 5/1994 | Romney | 482/124 |
| 5,716,307 | A * | 2/1998 | Vadher | 482/125 |
| 5,868,694 | A | 2/1999 | Marlow et al. | |
| 6,361,517 | B1 * | 3/2002 | Slinger | 602/28 |
| 6,544,152 | B2 | 4/2003 | Rosati | |
| 7,104,935 | B2 * | 9/2006 | Matsuoka | 482/124 |
| 7,189,192 | B2 | 3/2007 | Edgeton | |
| 7,241,252 | B1 * | 7/2007 | Gagliardi | 482/124 |
| 7,887,499 | B2 | 2/2011 | Cogswell | |
| 2003/0195092 | A1 * | 10/2003 | Basting | 482/124 |
| 2007/0028346 | A1 * | 2/2007 | Williams | 2/69 |
| 2008/0154165 | A1 * | 6/2008 | Ashihara et al. | 602/23 |
| 2011/0208242 | A1 * | 8/2011 | Hoffman et al. | 606/241 |

* cited by examiner

OTHER PUBLICATIONS

Office Action mailed Jul. 12, 2012, U.S. Appl. No. 12/944,234, filed Nov. 11, 2010.

*Primary Examiner* — Patricia Bianco
*Assistant Examiner* — Kari Petrik
(74) *Attorney, Agent, or Firm* — Harness, Dickey & Pierce, PLC

(57) ABSTRACT

A lumbar traction device is operable to be used by a user that has a lumbar region and a lower leg. The device includes a garment that includes at least one coupling member. The device also includes a lumbar support member operable to be worn adjacent to the lumbar region. The device also includes at least one lower leg support to be worn adjacent to the lower leg. Moreover, the device includes at least one connecting member connecting the lumbar support member and the lower leg support. The connecting member is substantially inelastic, and a load applied to the lower leg support is transferred to the lumbar support member via the connecting member to provide distraction to the lumbar region of the user. Moreover, the lumbar support member, the lower leg support, and/or the connecting member is coupled to the garment via the coupling member.

20 Claims, 7 Drawing Sheets

GARMENT WITH LUMBAR TRACTION DEVICE

CROSS-REFERENCE TO RELATED APPLICATIONS

This application is a continuation-in-part application of U.S. patent application Ser. No. 12/944,234, filed on Nov. 11, 2010, which claims the benefit of and priority to U.S. Provisional Application No. 61/260,649, filed on Nov. 12, 2009. The entire disclosure of each of the above applications is incorporated herein by reference.

FIELD

The present disclosure relates to a lumbar traction device and, more particularly to a garment with a lumbar traction device.

BACKGROUND

This section provides background information related to the present disclosure which is not necessarily prior art.

Back or lumbar pain is the second most common reason for doctor office visits in the United States after symptoms for the common cold. Furthermore, lumbar pain may severely limit the ability of the user to participate in work-related or leisurely activities. Thus, lumbar pain limits the productivity of users and excessively consumes medical resources.

Back pain is sometimes attributable to spinal stenosis, prolapsed or slipped discs and/or bulging discs. In addition to back pain, these conditions are known to also cause weakness or paralysis of muscles.

Lumbar traction or distraction is a well known and effective treatment for symptoms resulting from such conditions. Most lumbar traction kits rely on gravity, hydraulics, mechanical devices and/or elastic cords to work. These devices, however, may be too complex to use or too expensive for some patients. Also, with respect to lumbar traction kits having elastic (resilient) cords, the cords store energy such that when a load is removed from the elastic cord, the energy stored in the cord is transferred back to the spine, thereby cancelling out any alleviation of symptoms.

Thus, there is a need for a simple, cheap and effective lumbar traction device. While the traction kits described herein are not a solution to all forms of back pain and disability, the disclosed lumbar traction devices can offer an inexpensive and portable relief from back pain and disability.

Also, lumbar traction devices are typically bulky and can be difficult to set up (i.e., difficult to properly position on the body). Thus, there is also a need for a compact lumbar traction device that can be quickly and easily attached to the body and/or set up for use.

SUMMARY

A lumbar traction device is disclosed that is operable to be used by a user that has a lumbar region and a lower leg. The lumbar traction device includes a garment operable to be worn by the user, and the garment includes at least one coupling member. The lumbar traction device also includes a lumbar support member operable to be worn adjacent to the lumbar region of the user. The lumbar traction device also includes at least one lower leg support to be worn adjacent to the lower leg of the user. Moreover, the lumbar traction device includes at least one connecting member connecting the lumbar support member and the at least one lower leg support.

The connecting member is substantially inelastic, and a load applied to the at least one lower leg support is transferred to the lumbar support member via the at least one connecting member to provide distraction to the lumbar region of the user. Moreover, the lumbar support member, the lower leg support, and/or the connecting member is coupled to the garment via the at least one coupling member.

Also, a lumbar traction device is disclosed that is operable to be used by a user that has a lumbar region and a lower leg. The lumbar traction device includes a lumbar support member that is operable to be worn adjacent to the lumbar region of the user. The lumbar traction device includes at least one lower leg support to be worn adjacent to the lower leg of the user. Furthermore, the device includes at least one connecting member connecting the lumbar support member and the at least one lower leg support. The at least one connecting member is substantially inelastic. Moreover, the device includes an actuator operable to automatically push the at least one lower leg support in a direction away from the lumbar support member to tension the at least one connecting member and to provide distraction to the lumbar region of the user via the lumbar support member.

Still further, a lumbar traction device is disclosed that is operable to be used by a user that has a lumbar region, a first foot, and a second foot. The lumbar traction device includes a pair of pants operable to be worn by the user, wherein the pair of pants have an interior and an exterior. The lumbar traction device also includes a plurality of coupling members including a lumbar sleeve, a first connecting member sleeve, and a second connecting member sleeve. The lumbar sleeve, the first connecting member sleeve, and the second connecting member sleeve are disposed on an interior of the garment. The lumbar traction device also includes a belt with a lumbar support member operable to be worn adjacent to the lumbar region of the user. The device further includes a first shoe operable to be worn on the first foot of the user and a second shoe operable to be worn on the second foot of the user. The device further includes a first connecting member that is substantially inelastic. The first connecting member extends between and connects the first shoe to the belt such that a pushing load on the first shoe is transferred to the lumbar support member of the belt to provide distraction to the lumbar region of the user. Moreover, the device includes a second connecting member that is substantially inelastic. The second connecting member extends between and connects the second shoe to the belt such that a pushing load on the second shoe is transferred to the lumbar support member of the belt to provide distraction to the lumbar region of the user.

This section provides a general summary of the disclosure, and is not a comprehensive disclosure of its full scope or all of its features.

DRAWINGS

Figure 1:
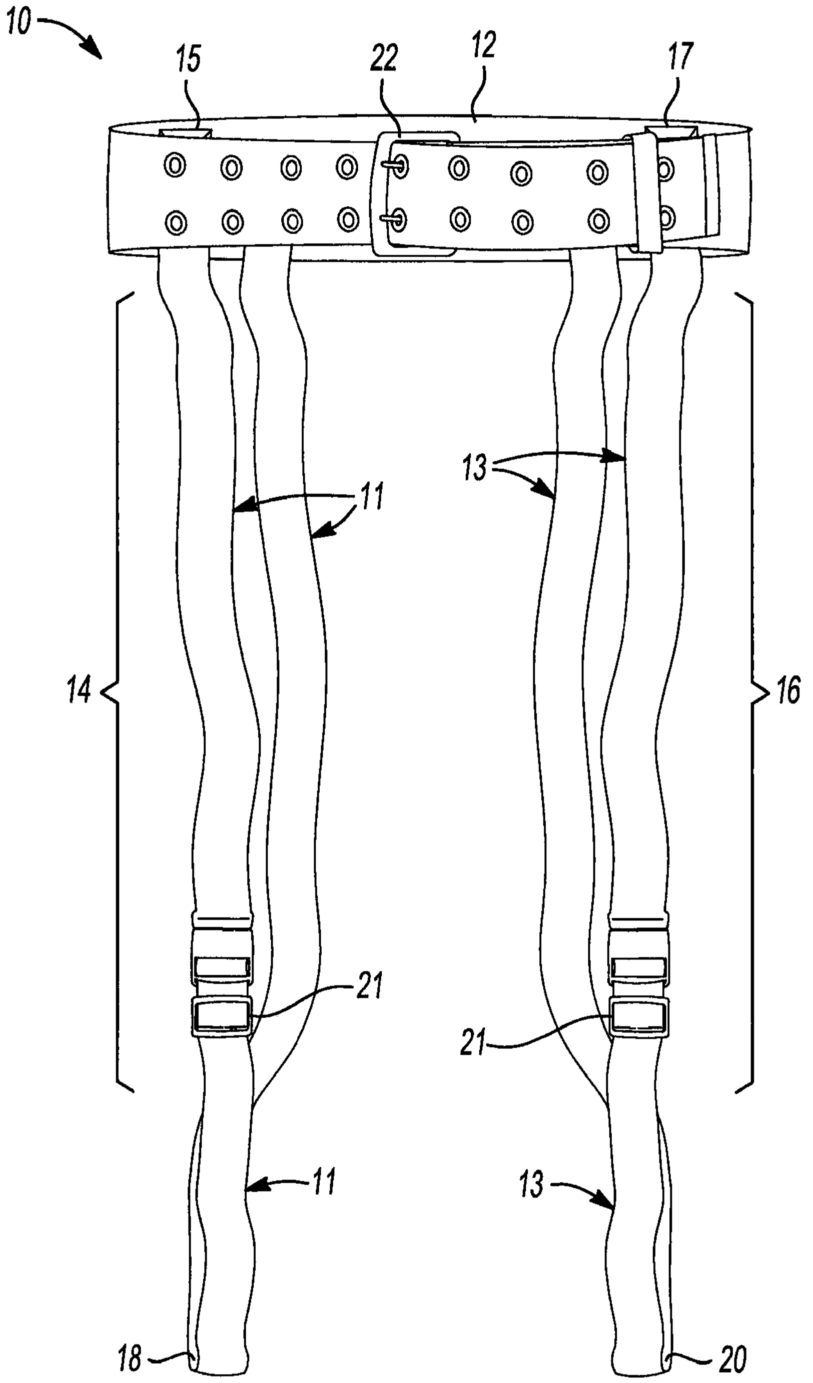
FIG. 1 is a front view of a lumbar traction device according to various teachings of the present disclosure.

The drawings described herein are for illustrative purposes only of selected embodiments of the present disclosure. Not all possible implementations are illustrated, and the drawings are not intended to limit the scope of the present disclosure. Corresponding reference numerals indicate corresponding parts throughout the several views of the drawings.

DETAILED DESCRIPTION

Example embodiments will now be described more fully with reference to the accompanying drawings.

FIG. 1 is a drawing illustrating an embodiment of the lumbar traction device 10. The lumbar traction device 10 can include a lumbar support member 12, which is worn adjacent to or around the back and lower abdomen and which rests, for instance, on the pelvic bone (e.g., on the ilium) of the user. The lumbar traction device 10 further includes at least one lower leg support 18 and 20 (i.e., lower extremity support, lower limb support, etc.). Furthermore, the device 10 includes at least one connecting member 14 and 16 connecting the at least one lower leg support 18 and 20 to the lumbar support member 12. As used herein, the term "lower leg" can include the region of a user below the knee of the user, including at least one of the shin/calf region, the ankle, and the foot of the user.

In some embodiments, the lumbar support member 12 is a belt that can extend continuously like a ring around the back and lower abdomen and can rest on the pelvic bone, as shown in FIG. 1. The lumbar support member 12 can also include a frame or ergonomic support for the lumbar region, and/or the lumbar support member 12 may be padded. The lumbar support member 12 can also include a fastener 22 for securing and/or tightening the lumbar support member 12 about the user. The fastener 22 can be of any suitable type, such as a buckle, prongs, snaps, buttons, Velcro, hooks, other types of fasteners, or combinations thereof. The lumbar support member 12 can be made of any flexible material that a user can wear. Also, the lumbar support member 12 can be substantially inelastic such that a longitudinal length of the lumbar support member 12 remains substantially constant even when under the influence of a longitudinal load. For instance, the belt may be composed of nylon, plastic, leather, or other materials.

In other embodiments, the lumbar support member 12 can be a frame or ergonomic support that does not fully enclose or encircle the user's waist. In these embodiments, the lumbar support member 12 can wrap or extend at least partially around the back or lower lumbar region of the user. Ends of the lumbar support member 12 can terminate on opposite lateral sides of the pelvis of the user. As will be described below, when the user applies a load to the lower leg support 18 the lumbar support member 12 forcibly presses against the user's lower lumbar region to provide distraction thereto.

Extending inferiorly from the lateral portions of the lumbar support member 12 are a first strap 11 and a second strap 13. The first strap 11 and second strap 13 include the first connecting member 14 and the second connecting member 16, respectively. In these embodiments, the straps 11 and 13 are U-shaped. The first strap 11 includes a first terminal end (not shown) and a second terminal end 15 attached to the anterior section and posterior section of the lumbar support member 12, respectively. The second strap 13 includes a first terminal end (not shown) and second terminal end 17 attached to anterior and posterior sections of the lumbar support member 12, respectively. The first strap 11 and second strap 13 are spaced apart laterally and are located at opposite ends of the lumbar support member 12. The first and second straps 11 and 13 further include the first lower leg support 18 and the second lower leg support 20, respectively. The connecting members 14 and 16 connect the lower leg supports 18 and 20 to the lumbar support member 12. The connecting members 14 and 16 are flexible and bendable, but are substantially inelastic, such that when a load is applied to the lower leg supports 18 and 20, the load is transferred to the lumbar support member 12 via the connecting members 14 and 16. As used herein "substantially inelastic" implies that when the load is applied to the lower leg supports 18 and 20 connecting members 14 and 16, the length (L) of the connecting members 14 and 16 does not substantially change. This means that the overall length (L) of the connecting members 14 and 16 will not increase by more than 0.5%. This definition can also apply for other components of the device 10 described as "substantially inelastic." In one embodiment the connecting members 14 and 16 and lower leg supports 18 and 20 are made of a substantially inelastic material such as a combination of polyester, nylon and polypropylene. In other embodiments, the connecting members 14 and 16 and lower leg supports 18 and 20 may be any other suitable substantially inelastic materials, such as lashing straps, chains, or ropes can be used, all of which can be purchased off the shelf.

In still other embodiments, the straps 11 and 13 are continuous loops (not shown), and the superior ends of the loops are connected to the lateral portions of the lumbar support member 12. The connecting members 14 and 16 portion of the straps 11 and 13 may be coupled to the lumbar support member 12 in any suitable fashion. For instance, the lumbar support member 12 may include receiving members for fixedly or removably attaching the loops thereto. Alternatively, the loops can be wrapped around the lumbar support member 12. It is envisioned that other means of connecting the loops to the lumbar support member 12 can be used as well. For instance, the superior ends of the connecting member can be sewn or stitched into the lumbar support member 12.

In some embodiments, the straps 11 and 13 can have a permanently fixed length. In other embodiments, the straps 11 and 13 can include one or more adjustment devices 21 for selectively changing the length of the straps 11 and 13. For instance, the adjustment devices 21 can be buckles, rectangular rings, or other known types for selectively lengthening and shortening the straps 11 and 13. It will be appreciated, however, that once the length of the straps 11 and 13 is selectively changed with the adjustment device 21, the length of the strap 11 and 13 will remain fixed during use (i.e., during distraction of the lumbar region of the user). Thus, the length of the straps 11 and 13 can be selectively changed with the adjustment devices 21 to accommodate taller users as well as shorter users as will be discussed below.

In other embodiments, the connecting members 14 and 16 can be non-continuous and include a first terminal end that is coupled to the lumbar support member 12 and a second terminal end that is coupled to a respective lower leg support 18 and 20. In these embodiments, the first terminal end of the connecting members 14 and 16 can be fixedly or removably attached to the corresponding lateral portion of the lumbar support member 12. For instance, the connecting members 14 and 16 may include a small continuous loop at the superior end of the strap that is sewn into or wrapped around the lumbar support member 12. Likewise, the second terminal end of the connecting members 14 and 16 can be fixedly or removably attached to the respective lower leg support 18 and 20.

More specifically, the lower leg supports 18 and 20 can be connected to or integral to the connecting members 14 and 16. In other embodiments, the lower leg supports 18 and 20 can be removably connected to the respective connecting members 14 and 16. The lower leg supports 18 and 20 are operable to receive a foot or feet of the user. The lower leg supports 18 and 20 may be the second distal end of the looped connecting member 14 and 16, as shown in FIG. 1, or may be any other structure sufficient to receive the foot, ankle, or calf region of a user. For instance, stirrups, shoes, socks, slippers, ankle bracelets, or the like may be connected to the distal end of the connecting members 14 and 16. In other embodiments, discussed further below, a foot bar may be interposed between the connecting members 14 and 16.

Figure 2:
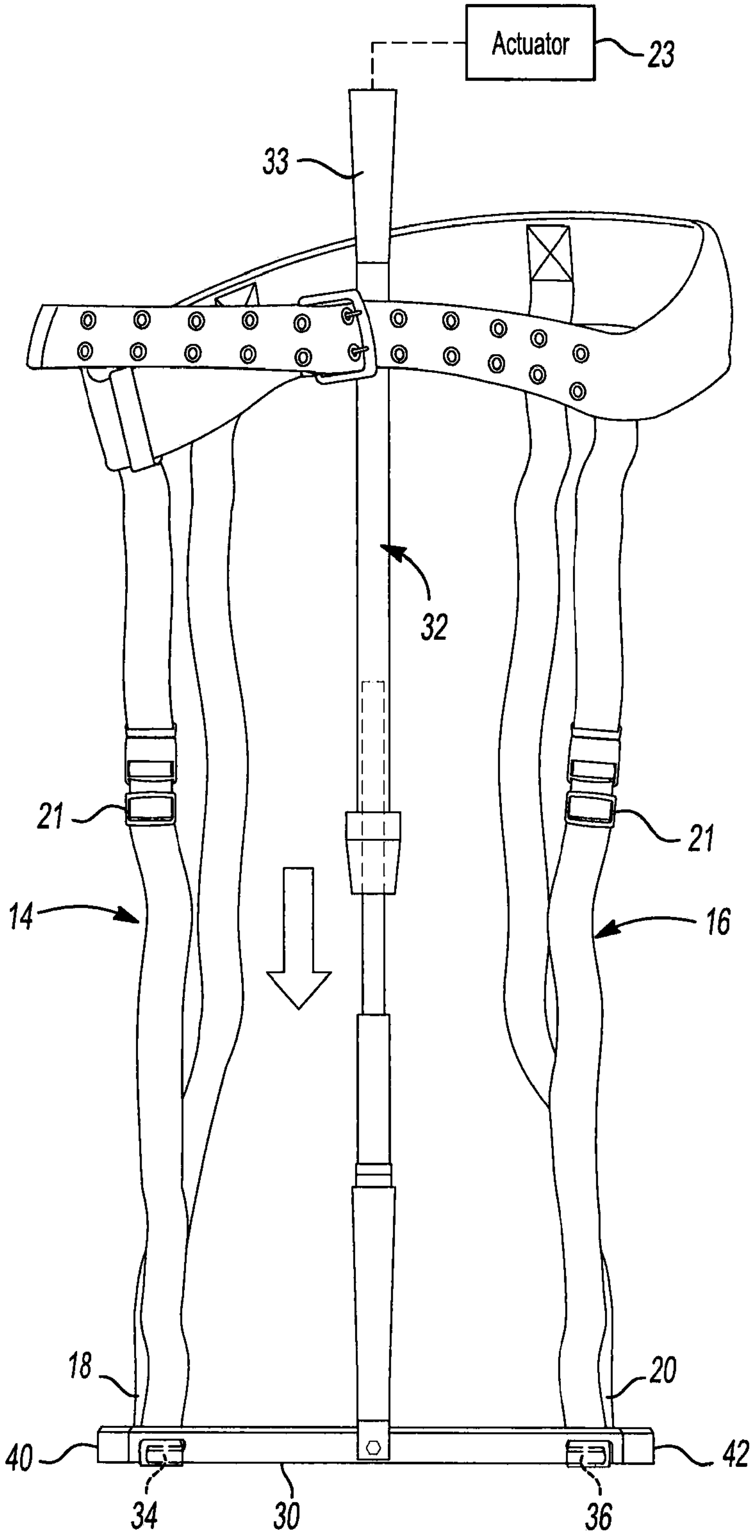
FIG. 2 is front view of additional embodiments of the lumbar traction device of the present disclosure.

FIG. 2 depicts an embodiment of the lumbar traction device in which a foot bar 30 is attached to and interposed between the first lower leg support 18 and the second lower leg support 18. The foot bar 30 can be attached to the first lower leg support 18 and the second lower leg support 20 in any suitable fashion. For instance, each end 40 and 42 of the foot bar 30 may be removably coupled to the lower leg supports 18 and 20, or permanently coupled thereto. Further shown in the depicted embodiment is an optional elongated rod 32 coupled to the foot bar 30, wherein the user applies an additional downward force to the rod to increase lumbar traction. The elongated rod 32 extends upward from a middle portion 35 of the foot bar 30.

Figure 3:
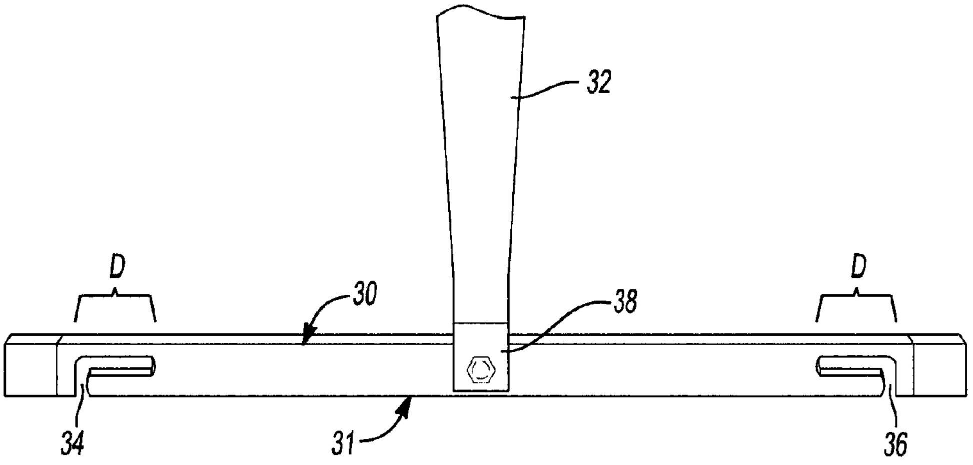
FIG. 3 is a detail view of an exemplary foot bar of the lumbar traction device of FIG. 2.

FIG. 3 depicts a front-view of an exemplary foot bar 30. The foot bar 30 includes a body 31, a first coupling portion 34 and a second coupling portion 36, for receiving the first and second lower leg supports 18 and 20, respectively. In some embodiments, the first and second coupling portions 34 and 26 are elongated slots. The foot bar 30 can further include an engaging member 38 that couples the elongated rod 32 (FIG. 2) to the middle portion 35 of the foot bar 30.

Exemplary foot bars 30 may be made of plastic, injection molded plastic, aluminum, steel, iron, or any other rigid material. The first and second coupling portions 34 and 36 are located at the lateral ends 40 and 42 of the foot bar 30. As mentioned, the first and second coupling portions 34 and 36 can be U-shaped slots. The slots have depths (D) sufficient to accommodate the respective lower leg support 18 and 20. While shown at the inferior of the foot bar 30, it is appreciated that the coupling portions 34 and 36 may be located at the superior of the foot bar 30. It is further envisioned that the coupling portions 34 and 36 can include additional components sufficient to secure the connecting members 14 and 16. In some embodiments, the coupling portions 34 and 36 may further include a securing member (not shown), such as a hinged latch, such that the lower leg support 18 or 20 is inserted in the coupling portions 34 or 36 and the spring loaded hinged latch secures the lower leg supports 18 or 20 therein. For instance, the spring loaded latch may be disposed at the opening of the coupling portions 34 or 36 of the foot bar 30, such that the lower leg support 18 or 20 is slid into the coupling portions 34 or 36 and secured by the latch, which is biased toward the closed position. While it is shown that the lower leg supports 18 and 20 are removably coupled to the foot bar 30, it is appreciated that in other embodiments the foot bar 30 is fixedly coupled to the lower leg supports 18 and 20. Also, it is appreciated that in other embodiments the lower leg supports 18 and 20 can include coupling portions sufficient to receive the foot bar 30.

Also shown in FIG. 3 is the engaging member 38. The engaging member 38 is a means for coupling the elongated rod 32 to the foot bar 30. The elongated rod 32 may be removably or fixedly coupled to the middle 35 of the foot bar 30. The engaging member 38 can be any structure sufficient to secure the elongate rod 32 to the body 31 of the foot bar 30. For instance, the engaging member 38 may be a receptacle that receives the elongated member. The receptacle can have depth sufficient to engage the elongated member. For instance, the receptacle may have a depth of 2-4 inches. It is appreciated that the depth, however, may be greater or less than the provided depth range. It is further noted that other engaging members 38 can be used. For example, the elongated rod 32 can have a threaded receptacle at the central axis of the distal end of the elongated rod 32 for receiving an engaging member 38, e.g. a bolt or screw. Alternatively, the foot bar 30 can include a threaded receptacle, such that a bolt or screw extending out of the central axis of the distal end of the elongated rod 32 threads into the threaded receptacle. It is envisioned that other means for securing the elongated rod 32 to the foot bar 30 are also sufficient. For instance, the elongated rod 32 may be permanently fixed (e.g., welded) to the foot bar 30. Also, in some embodiments, the rod 32 is coupled directly to one or both of the lower leg supports 18, 20, for instance, in cases where the device 10 does not include the foot bar 30.

Referring back to FIG. 2, the elongated rod 32 has length sufficient to extend from the foot bar 30 to within the reach of the user. In some embodiments, the elongated rod 32 can extend superiorly from a central area of the body 31 of the foot bar 30. The elongated rod 32 can be substantially perpendicular to the longitudinal axis of the foot bar 30. In some embodiments, the elongated rod 32 may be telescoping, such that the length can be selectively and telescopingly increased or decreased to thereby customize the length of the rod 32 for the particular user. Further, in some embodiments, the elongated rod 32 may have a handle 33 at an end proximate to the user. The user can grasp the handle 33 and can push downward on the foot bar 30, and the resulting load can be transferred to the lumbar support member 12 via the connecting members 14 and 16.

The handle 33 can include a high friction material, can include grips or recessed surfaces that mate with the user's hand, or can include other features for securing the user's grasp. Also, in some embodiments, the handle 33 can be substituted by a hook or other similar feature that receives the user's underarms (e.g., similar to crutches), the user's neck, or other body part, and that body part can be used to apply the load to the rod 32.

Additionally, in some embodiments, the rod 32 can be operably coupled to an actuator 23, which is shown schematically in FIG. 2. The actuator 23 can be of any suitable type, such as an electric motor, a hydraulic actuator, a pneumatic actuator, etc. In some embodiments, the actuator 23 can selectively telescopingly extend the rod 32 (e.g., via a screw-drive, etc.) or otherwise apply the load to the foot bar 30 to thereby push the foot bar 30 and lower leg supports 18, 20 away from the lumbar support member 12 to tension the connecting members 14, 16 and apply the distracting force to the lumbar region of the user.

As described, in some embodiments the foot bar 30 is interposed between the first and second connecting members 14 and 16 such that the connecting members 14 and 16 may be removably coupled to the foot bar 30. In these embodiments, the user may place one or both feet on the foot bar and apply a downward force to the foot bar 30. The foot bar 30 transfers the load to the lumbar support member 12 via the connecting members 14 and 16. Alternatively, the user can remove the foot bar 30 and place his feet at the lower leg supports 18 and 20 at the distal ends of the connecting members 14 and 16. As discussed, the foot bar 30 may be removably coupled to the first and second lower leg support 18 and 20. The foot bar 30 can be removed, such that the lumbar traction device is similar to the embodiments discussed above with respect to FIG. 1.

Figure 4:
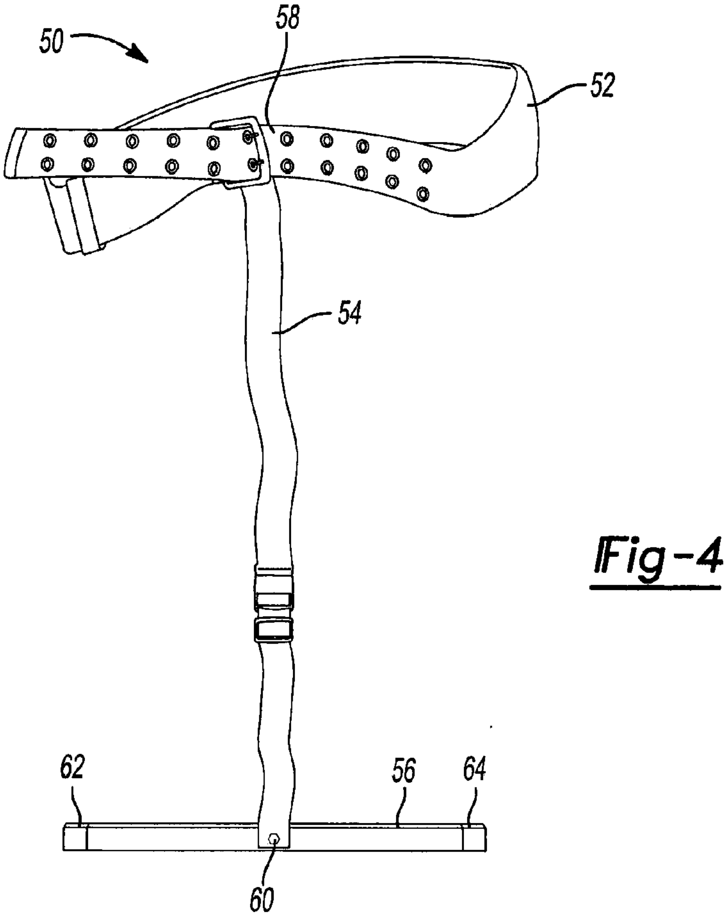
FIG. 4 is a front view of additional embodiments of the lumbar traction device of the present disclosure.

FIG. 4 illustrates an alternative embodiment of the lumbar traction device 50. In these embodiments, the lumbar traction device 50 is comprised of a lumbar support member 52, a foot bar 56, and a connecting member 54 connecting an anterior section 58 of the lumbar support member 52 and the foot bar 56. A fastener 60 attaches the connecting member 54 to the foot bar 56. It is envisioned that alternative means for affixing the foot bar 56 to the connecting means can be implemented as well. The connecting member 54 can be affixed to the lumbar support member 52 in the manner described above, with respect to FIGS. 1 and 2. For instance, the connecting member 54 can be stitched into the anterior section 58 of the lumbar support member or may loop around the anterior section 58 of the lumbar support member. It is envisioned that additional supports (not shown) may connect the distal ends 62 and 64 of the foot bar 56 to the connecting member 54.

A user can use the lumbar traction device 50 by wearing the lumbar support member 52 around his or her waist. The user places his or her feet at the distal ends 62 and 64 of the foot bar 56 and applying a downward force onto the foot bar 56. The downward force is transferred to the lumbar support member 52 via the connecting member 54.

It is appreciated that the lumbar support member 52 and the connecting member 54 can be substantially similar to the lumbar support member 12 and connecting members 14 and 16 described above. The foot bar 56 can also be substantially similar to the foot bar 30, described above. The foot bar 56 may further include a fastener 60 for connecting the connecting member 54 to the foot bar 56. Alternatively, the fastener 60 can be a hook or clip which receives the connecting member 54. It is envisioned that other connecting means sufficient to couple the fastener 60 to the foot bar 56 are also within the scope of the disclosure.

Figure 5:
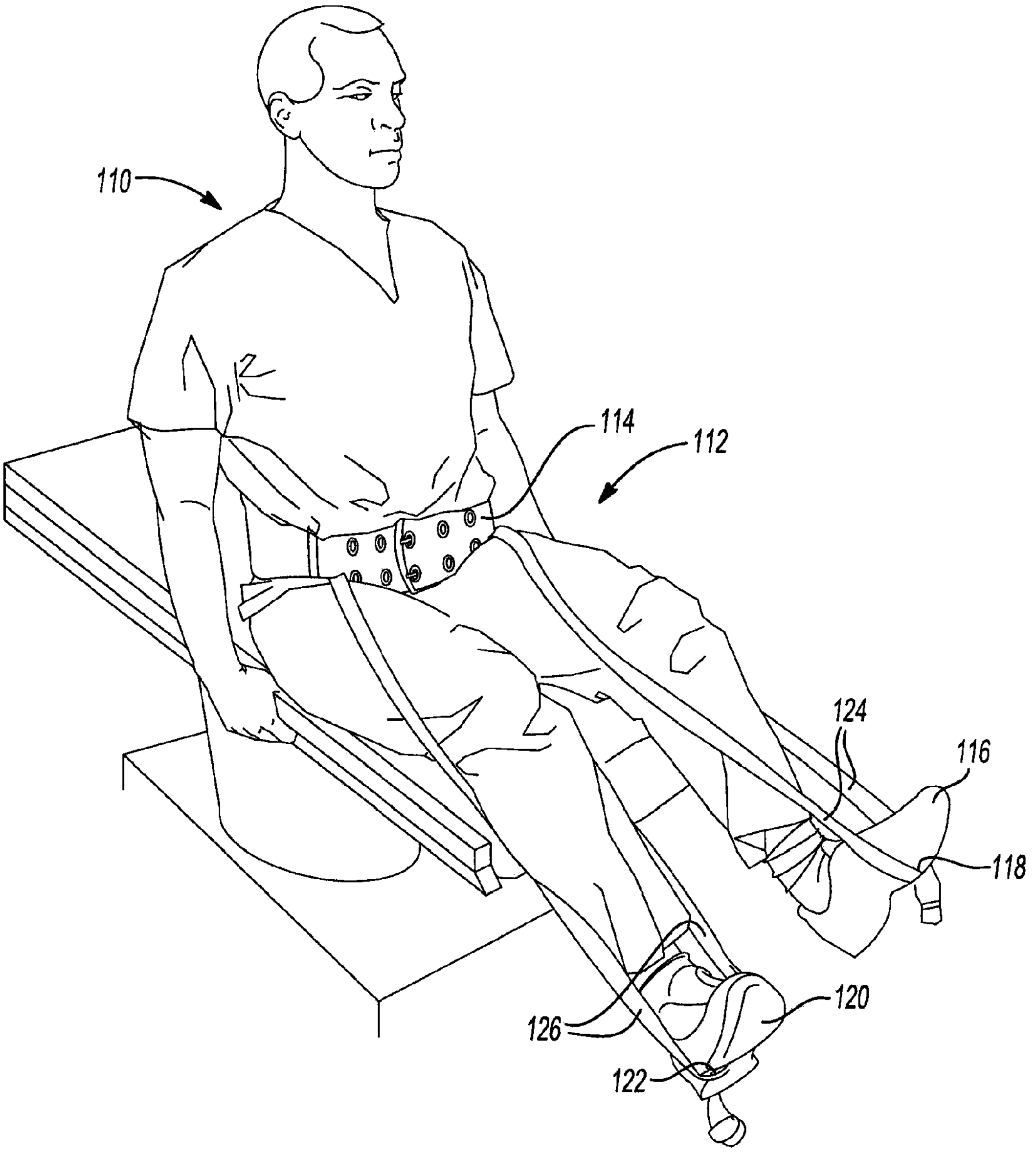
FIG. 5 is an isometric view of the lumbar traction device of FIG. 1 during use.

FIG. 5 illustrates an embodiment of the lumbar traction device 112 (e.g., the embodiments of FIG. 1) in use by a user 110. As can be seen, the user 110 is wearing the lumbar support member 114 around his waist. The user places his left foot 116 in a first lower leg support 118 and his right foot 120 in a second lower leg support 122. A first connecting member 124 connects the first lower leg support 118 to the lumbar support member 114 and a second connecting member 126 connects the second lower leg support 122 to the lumbar support member 114. The user 110 exerts a force on the lower leg supports 122 and 118 that is directed generally away from the lumbar support member 114. While recumbent, a pillow may be placed under the legs for support. By extending the hips and knees and plantar flexing of the feet at the first and second lower leg support 118 and 122, a load is transferred to the lumbar support member 114, which forcibly presses against the lower lumbar region of the user. As this occurs, the hip bone (pelvis) to which the sacrum is attached is distracted from the lumbar vertebrae i.e. pushed towards the feet, thereby relieving the pressure on the nerves in the lower back. As described, the connecting members 124 and 126 are substantially inelastic; therefore, when the user removes the downward force from the lower leg supports 122 and 118, no recoil is felt at the lumbar support member and the pelvis remains distracted from the vertebrae. Also, as described above, the lower leg supports 122 and 118 and lumbar support member 114 can be substantially inelastic; therefore, no recoil is felt once the user stops applying the downward force on the lower leg supports 122, 118.

Figure 6:
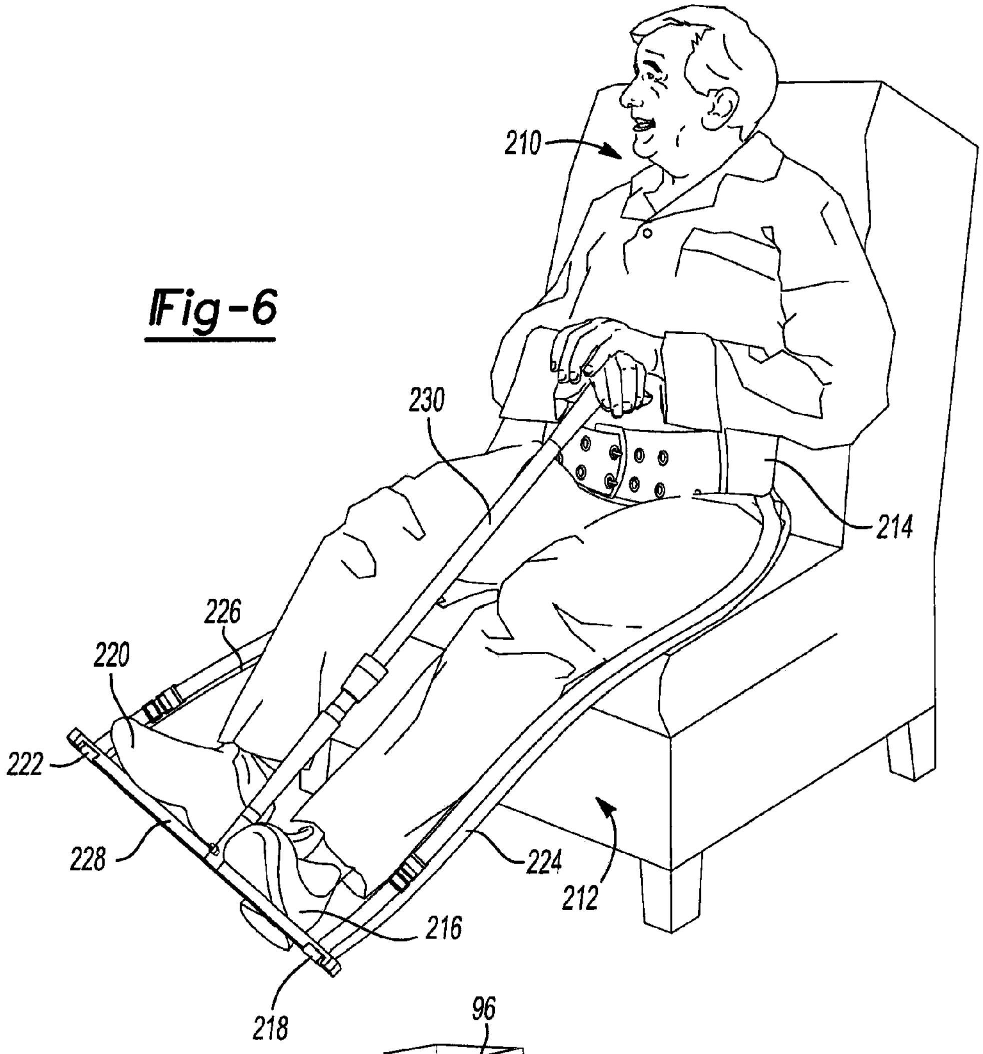
FIG. 6 is an isometric view of the lumbar traction device of FIG. 2 during use.

FIG. 6 illustrates an alternative embodiment of the lumbar traction device 212 (e.g., the embodiments of FIG. 2) in use by a user 210. As can be seen, the user 210 is wearing the lumbar support member 214 around his waist. The lumbar traction device 212 includes a foot bar 228, which connects the first lower leg support 218 and the second lower leg support 222. The user places his left foot 216 and right foot 220 on the foot bar 228 and applies a downward force to the foot bar 228 by flexing his knees and hips and flexing his feet 220 and 216. This will cause the force to be transferred to the lumbar support member 214, which causes the pelvis to be distracted from the lumbar vertebrae. Furthermore, the user 210 can apply a downward force to the foot bar 228 by pushing down axially on the elongate rod 230. The downward force applied to the foot bar 228 via the elongate rod 230 can be in addition to or in lieu of the downward force applied to the foot bar 228 via the user's feet 216 and 220.

As previously discussed, the connecting members 224 and 226, the lower leg supports 218 and 222, the foot bar 228, and the lumbar support member 214 can be substantially inelastic. Thus, there is very little energy stored in these components when the user exerts the downward force on the foot bar 228. Accordingly, when the patient stops applying the downward force to the foot bar 228, very little or no recoil is felt at the lumbar support member 214, thereby allowing the pelvis to remain distracted from the vertebrae.

Figure 7:
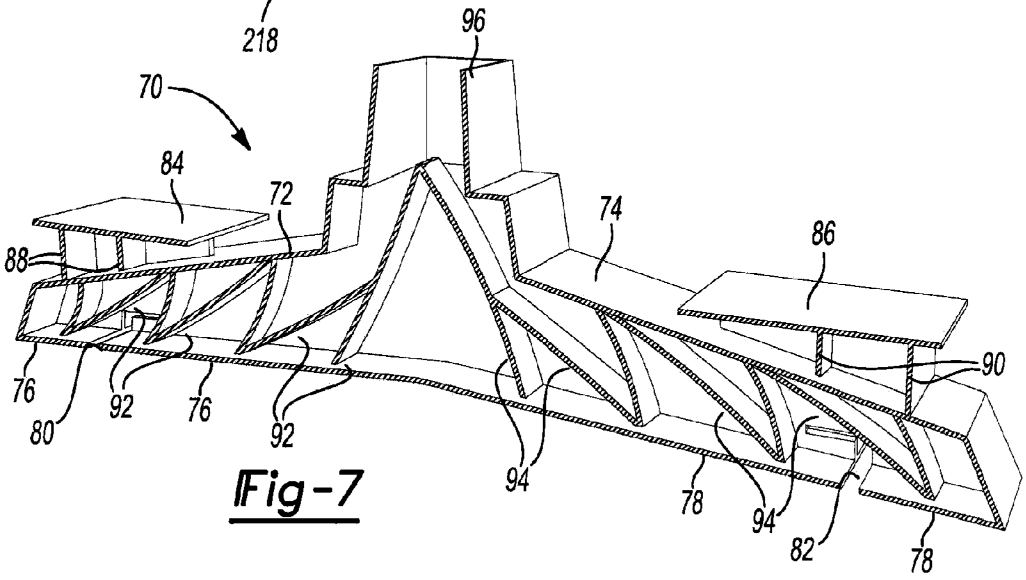
FIG. 7 is a section view of additional embodiments of the foot bar of the lumbar traction device of the present disclosure.

FIG. 7 illustrates a cross-sectional view of an alternative embodiment of a foot bar 70. The exemplary foot bar 70 includes a first superior extension 72, a second superior extension 74, a first inferior extension 76, and a second inferior extension 78. The first and second superior extensions 72 and 74 slope downward as the superior extensions 72 and 74 extend from the center of the foot bar 70. The first and second inferior extensions 76 and 78 are less sloped and extend from the center of the foot bar 70. It is appreciated that the inferior extensions 76 and 78 may have a slight upward or downward slope. Connecting the first superior extension 72 and the first inferior extension 76 are connected by a first plurality of ribs 92. In the exemplary embodiment, the ribs 92 are slanted, but it is appreciated that the ribs may also be substantially vertical as well. Similarly, the second superior extension 74 and the second inferior extension 76 are connected by a second plurality of ribs 94.

The foot bar 70 also includes a first coupling portion 80 and second coupling portion 82 for receiving the first and second connecting members 14 and 16, respectively. Coupling portions 80 or 82 can be a slot with sufficient depth to receive the respective connecting member. While shown as being located at the distal end of the inferior extensions 76 and 78, it is appreciated that the coupling portions 80 and 82 may be alternatively located at the superior extensions as well.

The exemplary foot bar 70 can also include a first foot rest 84 and a second foot rest 86, wherein the foot rests 84 and 86 are raised from the body of the foot bar 70. The first foot rest 84 can be supported by a third plurality of ribs 88, which extend in a substantially vertical manner from the first superior extension 82. Similarly, the second foot rest 86 can be supported by a fourth plurality of ribs 90, which extend in a substantially vertical manner from the second superior extension 84 ribs. The exemplary foot bar 70 can further include an engaging member 96 configured to receive the elongate rod. The engaging member 96 can be a rectangular opening with sufficient depth to receive the elongate rod. It is envisioned that in alternative embodiments, the engaging member 96 can also be a bolt or screw, which the elongate rod 32 can thread onto, or the engaging member 96 can include other sufficient means to connect the elongate rod 32 to the foot bar 70.

The exemplary foot bars 70 can be composed of plastic, injection molded plastic, aluminum, steel, iron, or any other rigid and inelastic material.

Figure 8:
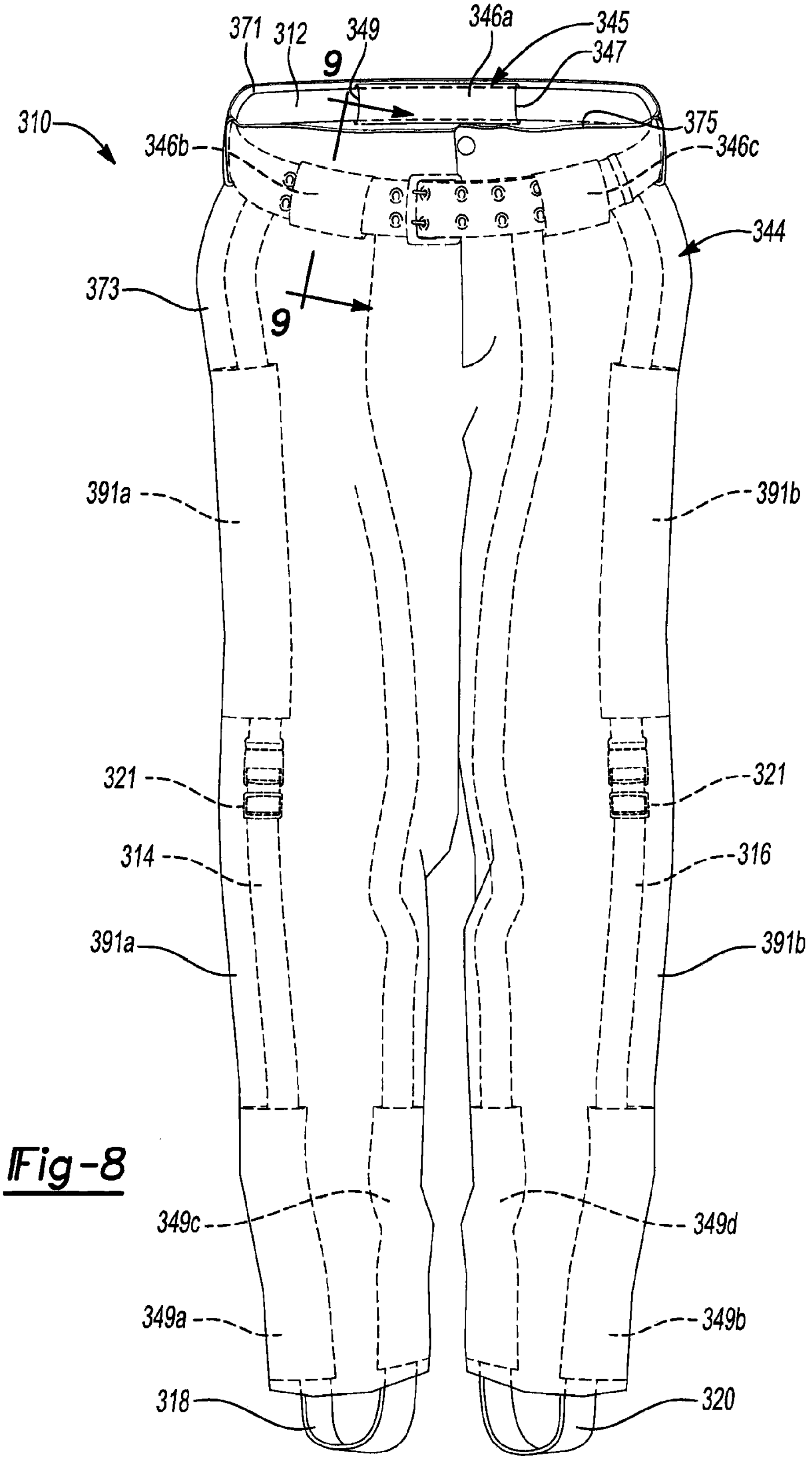
FIG. 8 is a front view of a garment with a lumbar traction device according to additional teachings of the present disclosure.
Figure 9:
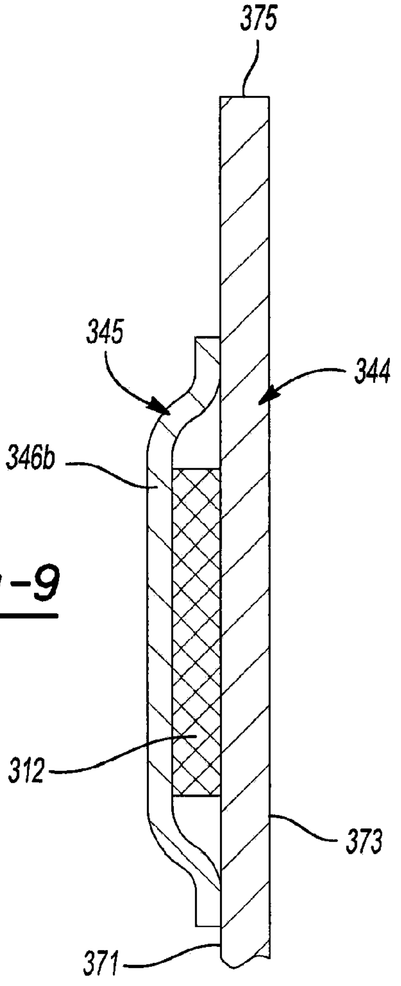
FIG. 9 is a section view of the garment and lumbar traction device taken along the line 9-9 of FIG. 8.

Referring now to FIGS. 8 and 9, additional embodiments of the lumbar traction device 310 are illustrated. Components that correspond to the embodiments of FIG. 1 are indicated with corresponding reference numbers increased by 300.

As shown, the device 310 can generally include a garment 344 with at least one coupling member 345. The garment 344 can be of any suitable type for wearing on the lower body of the user, such as a pair of pants, a pair of shorts, a skirt, etc. Also, the device 310 can include the lumbar support member 312, the connecting members 314, 316, and the lower leg supports 318, 320 described above. As will be discussed, the coupling member(s) 345 can operably couple the lumbar support member 312, the connecting members 314, 316, and/or the lower leg supports 318, 320 to the garment 344. As such, the lumbar traction device 310 can be comfortably worn, transported, and used by the user.

Although the lumbar support member 312, the connecting members 314, 316, and the lower leg supports 318, 320 shown in FIG. 8 are those of the embodiments of FIG. 1, it will be appreciated that any of the embodiments discussed above can be included. Also, it will be appreciated that any embodiments of the foot bar 30, 56, 70, 228 can be incorporated in the device 310 illustrated in FIG. 8.

In the embodiments illustrated, the garment 344 is a pair of pants that can be worn conventionally. The garment 344 can be made of cotton, polyester, or other flexible material. The garment 344 includes an interior 371 and an exterior 373. Also, as shown in FIGS. 8 and 9, the coupling member(s) 345 are included on the interior 371 of the garment 344 in the embodiments shown; however, it will be appreciated that the coupling member(s) 345 could be included on the exterior 373.

The coupling member(s) 345 can be of any suitable type, such as a sleeve with an open first end 347 and an open second end 349. More specifically, the coupling member 345 can comprise a piece of rectangular material (e.g., textile, cloth, etc.) that is secured to (e.g., by stitching, etc.) on two opposing sides such that the rectangular piece of material and the portion of the interior 371 of the garment 344 overlapped by the material cooperate to define the coupling member 345. The respective lumbar support member 312, connecting member 314, 316, or lower leg support 318, 320 can be received in and surrounded by the coupling member 345, and the respective lumbar support member 312, connecting member 314, 316, or lower leg support 318, 320 can extend through and out of both open ends 347, 349. Also, the lumbar support member 312, connecting member 314, 316, or lower leg support 318, 320 can move (e.g., slide) within the coupling member(s) 345, for example, during use such that the device 310 can be used without binding, pinching, or otherwise causing discomfort for the user.

It will be appreciated that there can be any number of coupling members 345, and the coupling members 345 can be included at any suitable location on the garment 344. For instance, in the embodiments shown in FIG. 8, there can be a plurality of coupling members 345, including a plurality of lumbar support sleeves 346*a*, 346*b*, 346*c*, a plurality of upper connecting member sleeves 348*a*, 348*b*, and a plurality of lower connecting member sleeves 349*a*, 349*b*, 349*c*, 349*d*.

The lumbar support sleeves 346*a*, 346*b*, 346*c* can be spaced apart from each other and disposed about a waist 375 of the garment 344. Specifically, the sleeve 346*a* can be substantially centered on the posterior of the garment 344, directly below the waist 375, and the sleeves 346*b*, 346*c* can be disposed on opposite lateral sides and spaced slightly below the anterior of the waist 375. The lumbar support sleeves 346*a*, 346*b*, 346*c* can receive the lumbar support member 312 to couple the lumbar support member 312 to the garment 344. Because of the positioning of the sleeves 346*a*, 346*b*, 346*c*, the lumbar support member 312 can be conveniently retained adjacent the user's lumbar region as intended when the garment 344 is worn.

The upper connecting member sleeves 348*a*, 348*b* can be disposed laterally on respective legs 391*a*, 391*b* of the garment. Likewise, the lower connecting member sleeves 349*a*, 349*b* can be disposed laterally on respective legs 391*a*, 391*b*. Moreover, the lower connecting member sleeves 349*c*, 349*d* can be disposed medially on respective legs 391*a*, 391*b*. The upper connecting member sleeves 348*a*, 348*b* can be disposed superior to the lower connecting member sleeves 349*a*, 349*b*. The upper and lower connecting member sleeves 348*a*, 348*b*, 349*a*, 349*b*, 349*c*, 349*d* can receive the connecting members 314, 316 to couple the connecting members 314, 316 to the garment 344. Thus, the connecting members 314, 316 are likely to be retained in a desirable position relative to the user's legs when the garment 344 is worn. Also, tangling of the connecting members 314, 316 is unlikely because the connecting members 314, 316 can be substantially secured in position relative to the garment 344.

Furthermore, as shown in the embodiments of FIG. 8, the lower leg supports 318, 320 can extend out of the garment 344 similar to stirrups. Thus, when the user puts on the garment 344, the user's feet can be received within the lower leg supports 318, 320, and the connecting members 314, 316 and lumbar support member 312 will likely be in the proper position on the user's body. Then, the user can proceed to use the device 310 as described above.

It will also be appreciated that a foot bar of the types discussed above could also be attached to the lower leg supports 318, 320 for use as described above. Likewise, the device 310 can be used with the rod 32 and/or the actuator 23 discussed above with respect to FIG. 2.

Also, in some embodiments, the garment 344 can be worn about in public even when the device 310 is not being used for treating lower back pain. For instance, the user can slip off the lower leg supports 318, 320 from the feet such that the supports 318, 320 hang freely. Otherwise, the user can selectively lengthen the connecting members 314, 316 (e.g., using the adjustment devices 321 included on the connecting members 314, 316) such that the user can walk or otherwise move freely without substantially tensioning the connecting members 314, 316.

Additionally, in some embodiments, the garment 344 can include a rope, a string or other similar means that can be used to pull the connecting members 314, 316 and the lower leg supports 318, 320 upwards for concealment inside the garment 344 when not in use for treating lower back pain. Also, the garment 344 can include a tie-down or other similar means for securing the connecting members 314, 316 and the lower leg supports 318, 320 inside the garment 344 when not in use.

Figure 10:
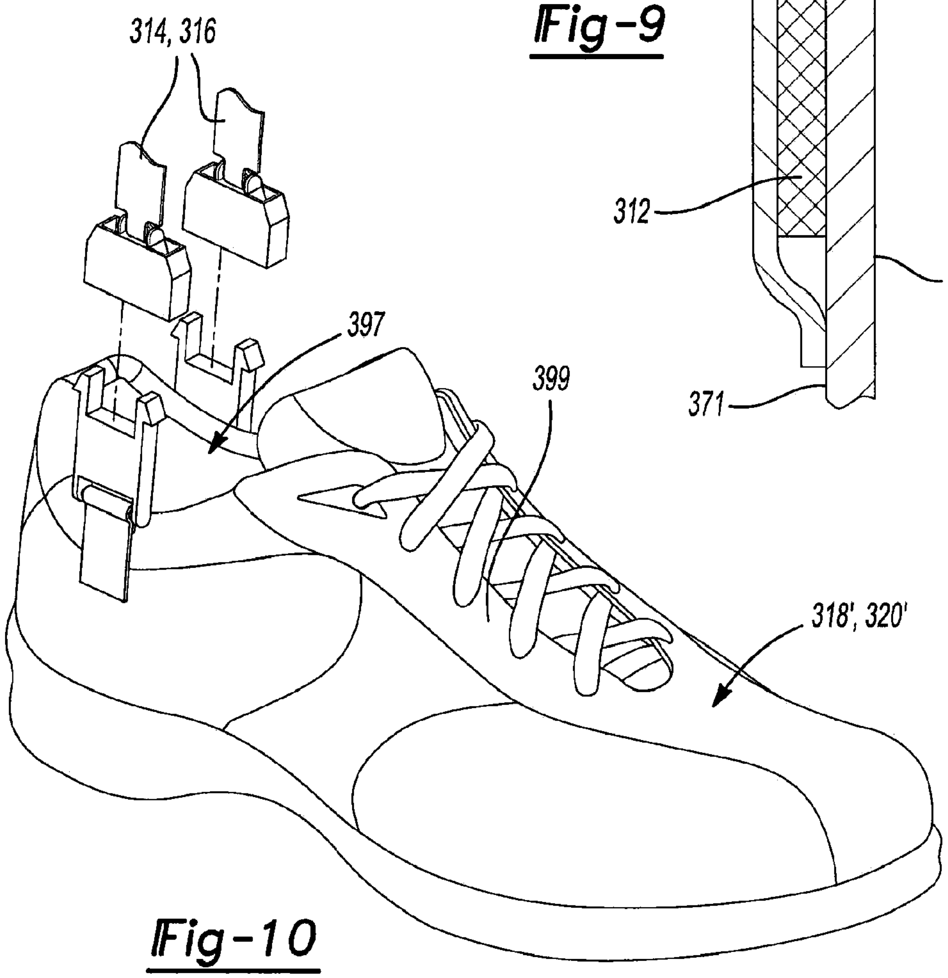
FIG. 10 is an isometric view of the lumbar traction device according to additional embodiments of the present disclosure.

Moreover, in additional embodiments illustrated in FIG. 10, the lower leg supports 318', 320' include articles of footwear 399 (e.g., shoes, boots, slippers, sandals, etc.) that define a respective cavity 397 for receiving the foot of the user. (Although only one article of footwear 399 is shown, it will be appreciated that both lower leg supports 318', 320' can include similar articles of footwear 399.) The footwear 399 can removably connect to the respective connecting member 314, 316. For instance, the footwear 399 and connecting members 314, 316 can include complimentary snap-fit buckles or other connectors for removably connecting the footwear 399 to the respective connecting member 314, 316.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A lumbar traction assembly operable to be used by a user that has a pelvic region with a groin area and a buttock area, the user also having a lumbar region that is superior relative to the buttock area of the pelvic region, the user further including a lower leg, the lumbar traction assembly comprising:

a garment adapted to cover the groin area and the buttock area of the pelvic region of the user and includes at least one coupling member fixed thereto; and a lumbar traction device that includes a lumbar support member operable to be worn adjacent to the lumbar region of the user, at least one lower leg support to be worn adjacent to the lower leg of the user, and at least one connecting member connecting the lumbar support member and the at least one lower leg support, the at least one connecting member being substantially inelastic, wherein a load applied to the at least one lower leg support is transferred to the lumbar support member via the at least one connecting member to provide distraction to the lumbar region of the user, wherein the at least one lower leg support includes a first lower leg support and a second lower leg support, and further comprising a foot bar that extends between and is coupled to both the first and second lower leg supports and a rod that is fixed to the foot bar and that extends away from the foot bar, the rod operable for pushing the foot bar and the first and second lower leg supports in a direction away from the lumbar support member to provide distraction to the lumbar region of the user, the at least one coupling member detachably couples the lumbar support member of the lumbar traction device to the garment.

2. The lumbar traction assembly of claim 1, wherein the at least one coupling member cooperates with a portion of the garment to form a sleeve with a first open end and a second open end, the sleeve continuously encircling and slidably coupled to the lumbar support member.

3. The lumbar traction assembly of claim 2, wherein the garment includes an interior and an exterior, and wherein the at least one coupling member is disposed on the interior of the garment.

4. The lumbar traction assembly of claim 1, wherein the at least one coupling member cooperates with a portion of the garment to form a sleeve and the sleeve slidably receives lumbar support member, thereby retaining the lumbar support member substantially adjacent the lumbar region of the user.

5. The lumbar traction assembly of claim 1, wherein the garment is at least one of a pair of pants, a pair of shorts, and a skirt.

6. The lumbar traction assembly of claim 1, wherein the lower leg includes a foot of the user, and wherein the lower leg support defines a cavity that receives the foot of the user.

7. The lumbar traction assembly of claim 6, wherein the connecting member is removably coupled to the lower leg support.

8. The lumbar traction assembly of claim 6, wherein the lower leg support includes an article of footwear.

9. The lumbar traction assembly of claim 1, wherein the at least one connecting member includes an adjustment device for selectively changing a length of the connecting member between a first fixed length and a second fixed length, the at least one connecting member being substantially inelastic at both the first fixed length and the second fixed length.

10. The lumbar traction assembly of claim 1, wherein the lumbar support member and the at least one connecting member are substantially inelastic.

11. The lumbar traction assembly of claim 1, further comprising an actuator that automatically pushes on the rod for pushing the foot bar and the first and second lower leg supports in the direction away from the lumbar support member.

12. A lumbar traction assembly operable to be used by a user that has a pelvic region with a groin area and a buttock area, the user also having a lumbar region that is superior relative to the buttock area of the pelvic region, the user further including a lower leg, the lumbar traction assembly comprising:

pants includes at least one coupling member fixed thereto; and a lumbar traction device that includes a lumbar support member operable to be worn adjacent to the lumbar region of the user, at least one lower leg support to be worn adjacent to the lower leg of the user, and at least one connecting member connecting the lumbar support member and the at least one lower leg support, the at least one connecting member being substantially inelastic, wherein a load applied to the at least one lower leg support is transferred to the lumbar support member via the at least one connecting member to provide distraction to the lumbar region of the user, wherein the at least one lower leg support includes a first lower leg support and a second lower leg support, and further comprising a foot bar that extends between and is coupled to both the first and second lower leg supports and a rod that is fixed to the foot bar and that extends away from the foot bar, the rod operable for pushing the foot bar and the first and second lower leg supports in a direction away from the lumbar support member to provide distraction to the lumbar region of the user, the at least one coupling member detachably couples the lumbar support member of the lumbar traction device to the pants.

13. The lumbar traction assembly of claim 12 wherein the at least one coupling member cooperates with a portion of the pants to form a sleeve with a first open end and a second open end, the sleeve continuously encircling and slidably coupled to the lumbar support member.

14. The lumbar traction assembly of claim 12 wherein the at least one coupling member cooperates with a portion of the pants to form a sleeve and the sleeve slidably receives lumbar support member, thereby retaining the lumbar support member substantially adjacent the lumbar region of the user.

15. The lumbar traction assembly of claim 13 wherein the pants includes an interior and an exterior, and wherein the at least one coupling member is disposed on the interior of the pants.

16. The lumbar traction assembly of claim 12 wherein the lower leg includes a foot of the user, and wherein the lower leg support defines a cavity that receives the foot of the user.

17. The lumbar traction assembly of claim 16 wherein the connecting member is removably coupled to the lower leg support.

18. The lumbar traction assembly of claim 16 wherein the lower leg support includes an article of footwear.

19. The lumbar traction assembly of claim 12 wherein the at least one connecting member includes an adjustment device for selectively changing a length of the connecting member between a first fixed length and a second fixed length, the at least one connecting member being substantially inelastic at both the first fixed length and the second fixed length.

20. The lumbar traction assembly of claim 12 wherein the lumbar support member and the at least one connecting member are substantially inelastic.

* * * * *